(12) United States Patent
Moehring et al.

(10) Patent No.: US 10,660,604 B2
(45) Date of Patent: May 26, 2020

(54) APPARATUS AND METHOD FOR CHARACTERIZATION OF ACUTE OTITIS MEDIA

(71) Applicant: Otonexus Medical Technologies, Inc, Seattle, WA (US)

(72) Inventors: Mark A. Moehring, Seattle, WA (US); George A. Gates, Boerne, TX (US); Daniel M. Kreindler, Foster City, CA (US); Jay A. Chesavage, Palo Alto, CA (US); Rahul Singh, Carlsbad, CA (US)

(73) Assignee: OtoNexus Medical Technologies, Inc., Seattle, WA (US)

( * ) Notice: Subject to any disclaimer, the term of this patent is extended or adjusted under 35 U.S.C. 154(b) by 1100 days.

(21) Appl. No.: 14/797,181

(22) Filed: Jul. 13, 2015

(65) Prior Publication Data
US 2017/0014053 A1    Jan. 19, 2017

(51) Int. Cl.
*A61B 8/00* (2006.01)
*A61B 8/12* (2006.01)
*A61B 5/12* (2006.01)
*A61B 8/08* (2006.01)

(52) U.S. Cl.
CPC ............... *A61B 8/12* (2013.01); *A61B 5/126* (2013.01); *A61B 8/085* (2013.01); *A61B 8/4427* (2013.01); *A61B 8/4444* (2013.01); *A61B 8/488* (2013.01); *A61B 8/5223* (2013.01)

(58) Field of Classification Search
CPC .................................... A61B 8/00; A61B 5/00
See application file for complete search history.

(56) References Cited

U.S. PATENT DOCUMENTS

| | | | |
|---|---|---|---|
| 4,442,715 A | 4/1984 | Brisken | |
| 5,105,822 A | 4/1992 | Stevens | |
| 5,699,809 A * | 12/1997 | Combs | A61B 5/121 600/558 |
| 5,800,336 A * | 9/1998 | Ball | H04R 25/606 600/25 |
| 5,825,894 A | 10/1998 | Shinnib | |

(Continued)

FOREIGN PATENT DOCUMENTS

| | | |
|---|---|---|
| CN | 104568736 A | 4/2015 |
| WO | WO-2016052817 A1 | 4/2016 |
| WO | WO-2017011035 A1 | 1/2017 |

OTHER PUBLICATIONS

"PCT/US16/19432 International Search Report dated May 11, 2016".

(Continued)

*Primary Examiner* — Joel F Brutus
(74) *Attorney, Agent, or Firm* — Wilson Sonsini Goodrich & Rosati

(57) ABSTRACT

An ultrasound signal processor uses an excitation generator to cause displacement of a tympanic membrane while a series of ultrasound pulses are applied to the tympanic membrane. Phase differences between a transmitted signal and received signal are examined to determine the movement of the tympanic membrane in response to the applied excitation. An examination of the phase response of the tympanic membrane provides a determination as to whether the fluid type behind the tympanic membrane is one of: no fluid, serum fluid, or purulent fluid.

31 Claims, 7 Drawing Sheets

(56) References Cited

U.S. PATENT DOCUMENTS

| | | | |
|---|---|---|---|
| 6,048,320 A | 4/2000 | Brainard | |
| 6,093,150 A | 7/2000 | Chandler | |
| 6,312,379 B1 | 11/2001 | Bradley et al. | |
| 6,354,999 B1 | 3/2002 | Dgany et al. | |
| 6,951,127 B1 | 10/2005 | Bi et al. | |
| 7,107,159 B2 | 9/2006 | German et al. | |
| 7,440,117 B2 | 10/2008 | Degertekin et al. | |
| 9,074,976 B2 | 7/2015 | Adolphi et al. | |
| 9,482,646 B2 | 11/2016 | Nagae et al. | |
| 9,636,015 B2 | 5/2017 | Hadba et al. | |
| 9,726,647 B2 | 8/2017 | Walker et al. | |
| 2004/0167404 A1 | 8/2004 | Bessler | |
| 2006/0070424 A1* | 4/2006 | Saari | G01L 1/26 73/1.08 |
| 2007/0016050 A1* | 1/2007 | Moehring | A61B 8/06 600/454 |
| 2007/0129632 A1* | 6/2007 | Voie | A61B 5/6817 600/438 |
| 2008/0051655 A1 | 2/2008 | Sato | |
| 2009/0143656 A1* | 6/2009 | Manwaring | A61B 5/026 600/324 |
| 2010/0069752 A1* | 3/2010 | Lewandowski | A61B 5/121 600/438 |
| 2010/0191144 A1 | 7/2010 | Zoth et al. | |
| 2010/0272299 A1* | 10/2010 | Van Schuylenbergh | H04R 25/554 381/315 |
| 2013/0303941 A1* | 11/2013 | Porges | A61B 5/125 600/559 |
| 2014/0323862 A1 | 10/2014 | Silverman et al. | |
| 2015/0110333 A1* | 4/2015 | Norris | H04R 19/02 381/394 |
| 2015/0133746 A1 | 5/2015 | Oyadiran et al. | |
| 2016/0128558 A1 | 5/2016 | Larin et al. | |
| 2016/0367143 A1 | 12/2016 | Catheline et al. | |

OTHER PUBLICATIONS

International Search Report for PCT/US2018/042138—dated Oct. 22, 2018.
Office Action dated Jul. 26, 2018 for U.S. Appl. No. 15/173,615.
Final Office action dated Mar. 21, 2019 for U.S. Appl. No. 15/173,615.
Office action dated Jul. 18, 2019 for U.S. Appl. No. 15/173,615.

\* cited by examiner cross section C-C view at TM

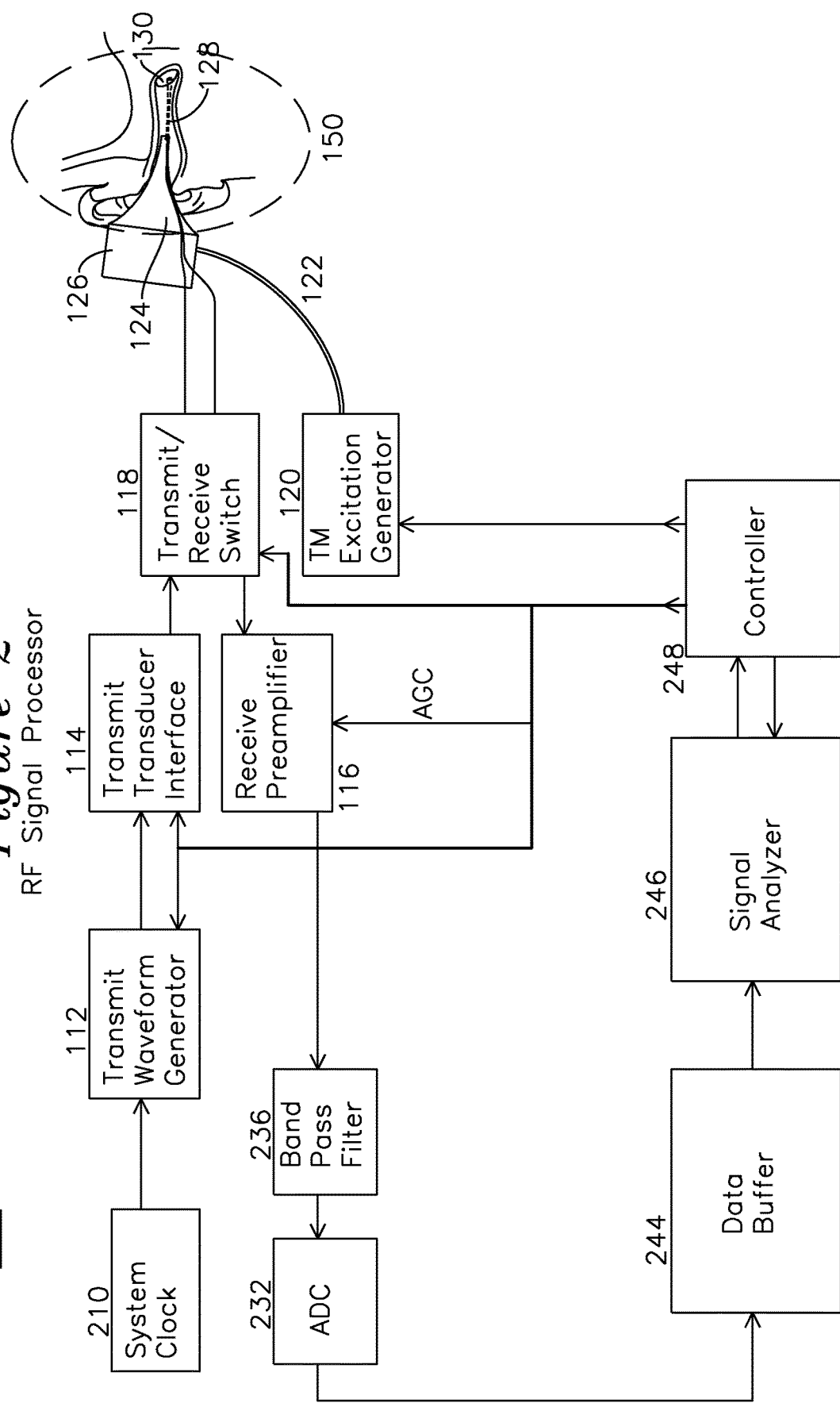

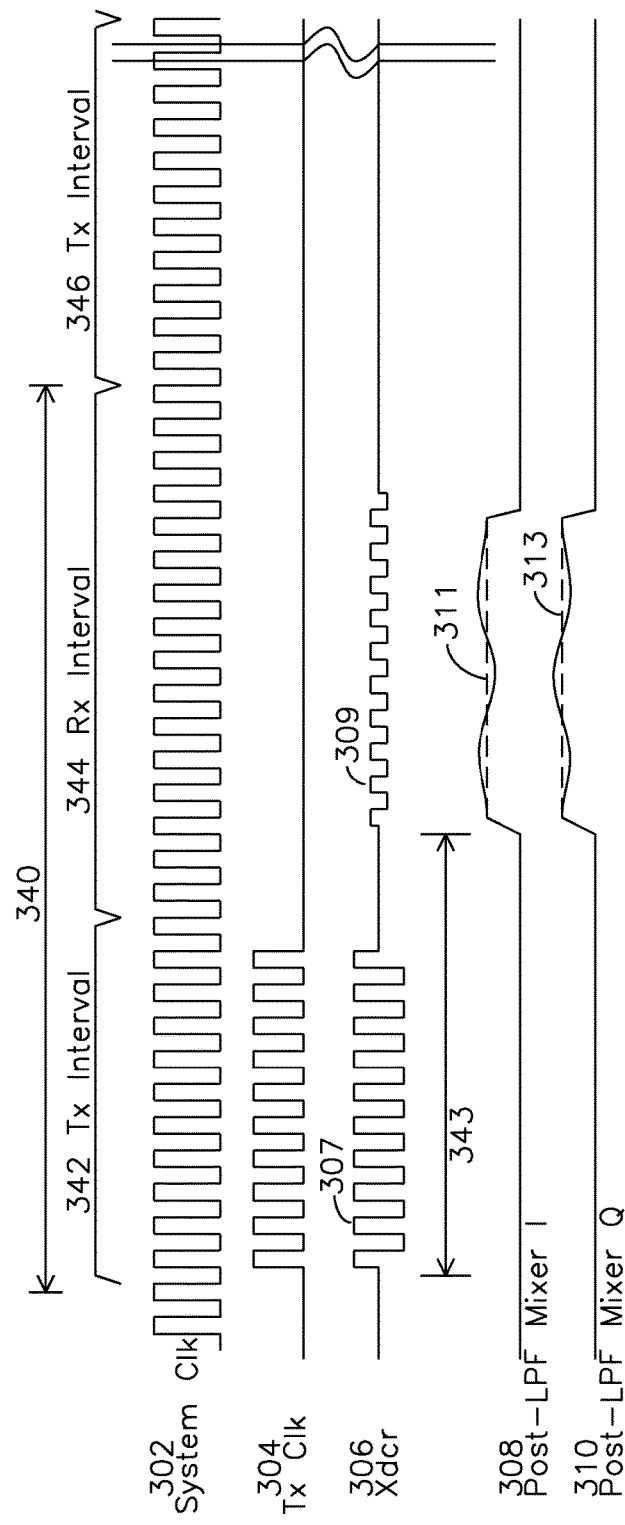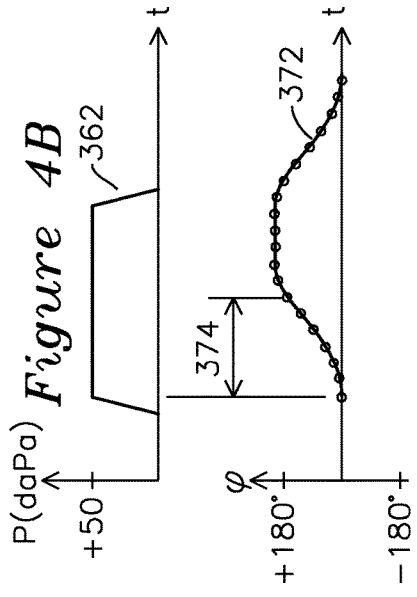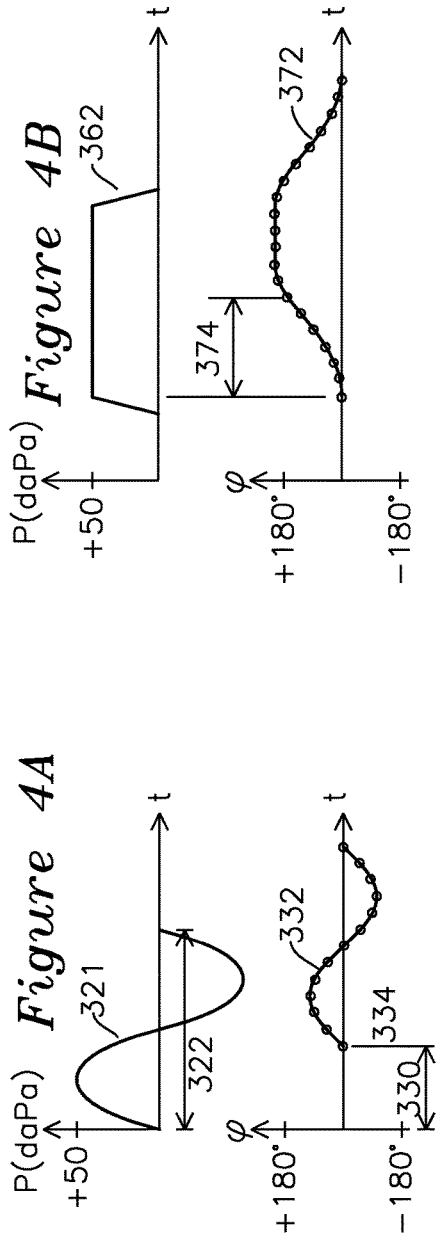

Input signal phase

Sampled TM Displacement w/phase wrap

Unwrapped phase estimate

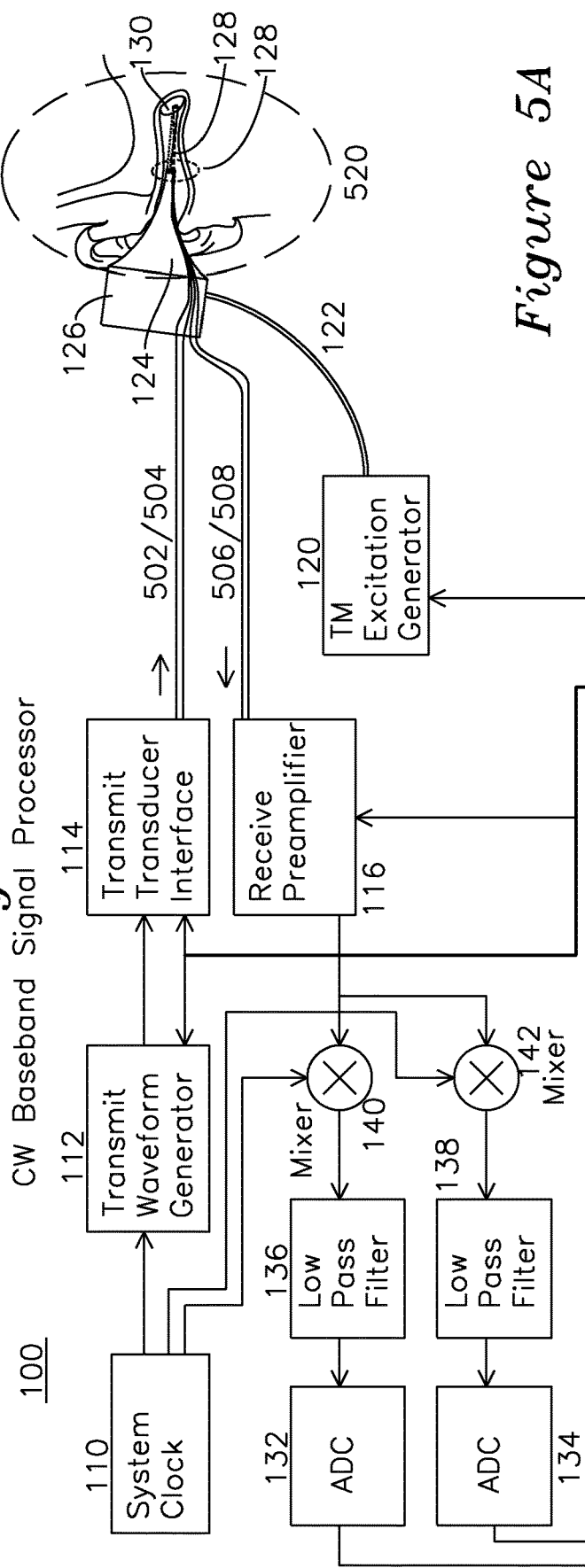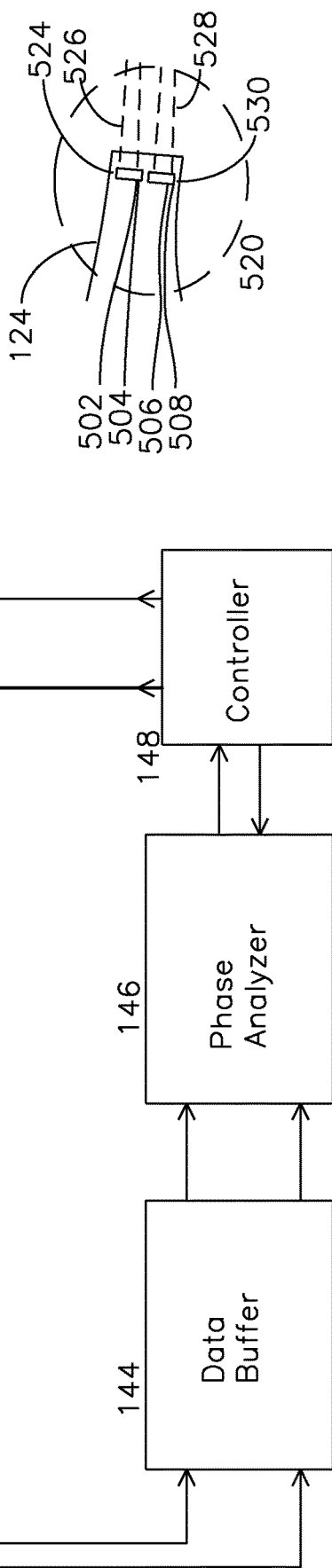
Figure 5
Figure 5A

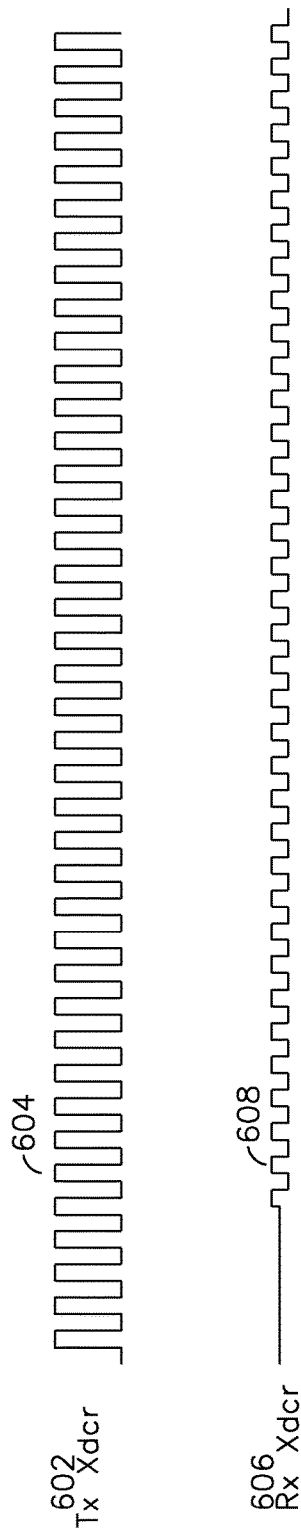
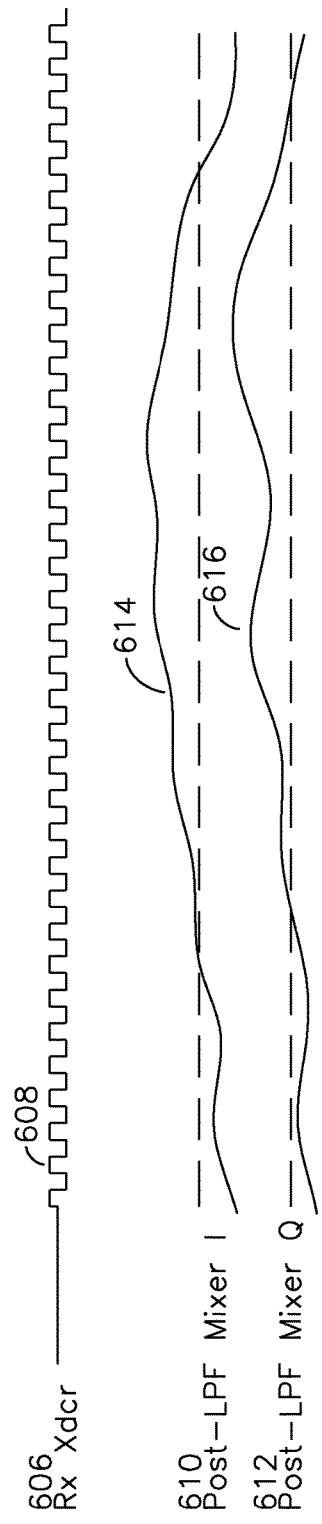
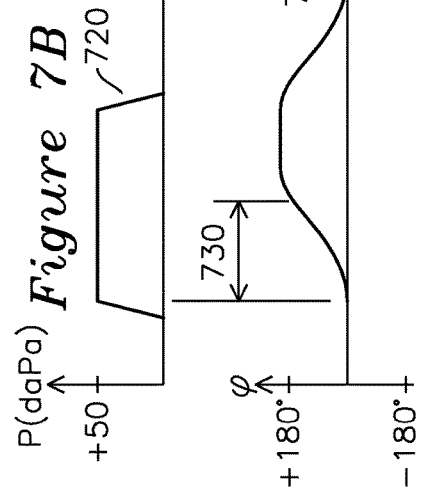
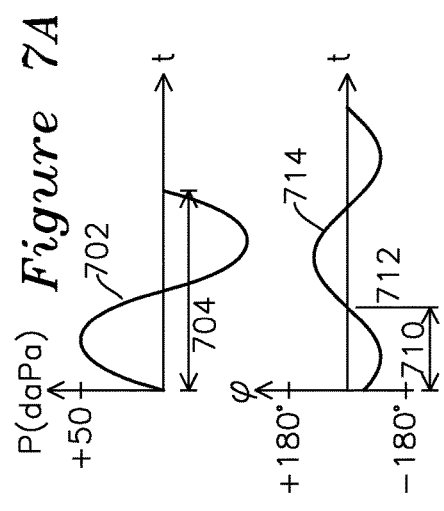

APPARATUS AND METHOD FOR CHARACTERIZATION OF ACUTE OTITIS MEDIA

FIELD OF THE INVENTION

The present invention relates to a device for the detection of middle ear effusion with discrimination of fluid type. In particular, the invention relates to the characterization of middle ear effusion behind the tympanic membrane by stimulating the tympanic membrane using a low frequency excitation such as acoustic and measuring the displacement behavior with a comparatively higher frequency excitation such as ultrasound.

BACKGROUND OF THE INVENTION

Acute otitis media (AOM) is an inflammatory process in the middle ear and is the most common clinical condition seen by pediatricians in children fifteen years and younger. AOM is generally associated with the presence of a middle ear effusion and is considered a middle ear inflammation. Complications of undiagnosed AOM can include hearing loss. Left untreated in children, recurrent AOM can also lead to delays in the development of speech and language skills.

There are two key factors in the diagnosis of AOM: detection of the presence of effusion, and characterization of the type of effusion as either serous, mucoid, purulent or combinations of these. Decision by the health care provider regarding appropriate treatment relies on confirmation of both the presence of effusion and its type. Health care practitioners use a variety of tests to evaluate a patient suspected of having AOM. The only definitive tests for AOM are myringotomy and tympanocentisis, procedures which involve direct aspiration of fluid from the middle ear by puncturing the tympanic membrane and drawing fluid, followed by visual and biochemical analysis of the fluid. These are invasive procedures performed in a surgical setting under anesthesia. Because they are invasive and have significant associated risks of complications, myringotomy and tympanocentisis are not used as standard diagnostic methods for AOM except in research settings.

Several other non-invasive diagnostic tests are available for evaluating AOM, including acoustic reflectometry, tympanometry, pneumatic otoscopy, and otoscopy, however, none of these tests achieves the diagnostic accuracy of invasive myringotomy and tympanocentisis; the overall likelihood of obtaining an accurate diagnosis using any of the non-invasive methods is no better than 50%. More importantly, the various non-invasive methods are useful only in identifying the presence of middle ear effusion; they provide no information regarding the type of effusion. Because of the risks associated with undiagnosed AOM, and the recognized unreliability of the non-invasive diagnostic tests, patients who are diagnosed with middle ear effusions based on any of these non-invasive tests are often prescribed antibiotics. In many instances, these patients do not have AOM. In addition to the increased cost burden of unnecessary antibiotic treatment, the patients are exposed to the side effects of antibiotics and the attendant and significant risk of developing antibiotic resistance.

Acute otitis media is one of the most common causes of childhood health issues, which include for example, bacterial infections, antibiotic overuse, hearing loss, and surgeries. AOM is responsible for more than 12 million office visits nationwide per year, accounting for over 50 percent of all pediatric antibiotic prescriptions and as much as $5 billion in annual costs. The number of operative procedures performed due to unresolved AOM in the United States is estimated at about 600,000 per year.

The majority of children have at least one episode of AOM by the time they are two years of age. AOM is characterized by ear pain, fever, occasional rupture of the ear drum, and findings of middle ear inflammation, including fluid in the middle ear. About 10 percent of children have recurrent AOM, and these children account for around 40 percent of all AOM episodes. The prevalence of AOM in the United States is increasing. Thus, current diagnostic and treatment methods are not lowering the rate of AOM in the United States.

OM is fundamentally defined by the presence of an effusion in the middle ear. In AOM, the middle ear effusion ("MEE") is induced by infective agents and is often thin or serous with viral infection and thicker and purulent with bacterial infection. Acute MEE may persist, even with appropriate antimicrobial treatment. After 30 days, the MEE is termed as chronic, and the condition is referred to most commonly as otitis media with chronic effusion or "OME." Chronic MEE may be thin and watery, purulent, or, most commonly, thick and mucoid. Mucoid effusion is the hallmark of OME and is often called "glue ear" because of its high viscosity. Because each type of MEE has a different prognosis and treatment, the ability to delineate the type of the effusion is of great clinical value.

In spite of decades of research, optimal management of OM remains controversial. In a recent prospective study, antibiotic treatment of OM accounted for more than 90 percent of all antibiotic use during the first two years of life. It has been estimated that distinguishing AOM from OME and deferring antibiotics for OME would avoid 6 to 8 million courses of unnecessary antibiotic therapy annually. While antibiotics reduce pain symptoms in AOM, their widespread use in AOM has led to an alarming increase in the prevalence of resistant organisms worldwide without any substantial decrease in complications or sequelae of AOM. Given the high spontaneous resolution rate of AOM, there are serious questions about the need for antibiotics in most cases. Thus, physicians and parents are frequently uncertain about proper treatment because there are no clear-cut clinical findings that might reliably predict which cases will resolve spontaneously and which cases would be better treated with an oral antibiotic. The recent American Academy of Pediatrics 2014 guideline recommended withholding antibiotic when uncertainty exists but did not discuss ways and means to implement the guideline.

Many children with fever and a red tympanic membrane ("TM") have no MEE and thus do not have AOM. These children do not benefit from antimicrobial therapy, even though many receive it as a precaution.

Similar considerations apply to cases of persistent MEE (OME). Detecting MEE is difficult without expensive equipment, such as a tympanometer or an audiometer. While screening tympanometers are available, they are not widely used in primary care offices where the majority of cases of AOM/OME are first seen. Acoustic reflectometry was introduced 15 years ago as a method for primary physicians and parents to indicate MEE presence. Although the sensitivity and specificity of acoustic reflectometry is similar to that of tympanometry, neither device will predict which cases may resolve spontaneously and which cases will require treatment. Moreover, neither device is widely used in primary care offices. Chronic MEE is therefore under-diagnosed in primary care practice.

OME may cause hearing loss without other symptoms. The adverse effects of OME on hearing and on the development of cognitive, linguistic, additive, and communicative skills are of concern to parents and physicians alike. National guidelines recommend waiting 3 to 6 months before surgical removal of the MEE and insertion of a ventilation tube. Some effusions cause substantial hearing loss. Typically, middle ears that are impacted with the characteristic viscous effusion (glue ear) are associated with substantial hearing loss that may persist for years. Primary care physicians, unlike ENT specialists, lack a robust clinical method that can distinguish between a mucoid effusion (glue ear) and one that contains a serous (watery) effusion, which is more likely to resolve spontaneously.

One of the major sources of controversy about OM in clinical practice is accuracy of diagnosis. Otoscopy, the key examination technique, is a visual inspection of the TM by which one may deduce the normal or abnormal middle ear. The equipment and skills for otoscopy are variable. Although with practice, many physicians become proficient otoscopists, a monocular examination of the TM of a struggling infant through a tiny speculum remains a difficult and challenging maneuver. Often only a glimpse of the TM is possible. Use of the binocular operating microscope, which permits a 3D view of the TM, is the most precise method of otoscopy and is widely used by ear, nose, and throat specialists. However, this expensive equipment is rarely found in primary care practices where the majority of AOM diagnoses are made. Accordingly, only 40 percent of primary care pediatricians are confident about their otoscopic findings.

The essential elements of otoscopy are a description of: (1) the static characteristics of the TM (color, position, translucency), (2) the contents of the middle ear (air, ear effusion, other), and (3) the mobility of the TM in response to externally applied air pressure (pneumatic otoscopy). Determining the presence of effusion (liquid) in the middle ear is the critical variable in making a diagnosis of OME. Given that the effusion may vary in amount and consistency from case to case and may be obscured by the condition of the TM, it is fair to say that even when done under ideal conditions (binocular microscope, pneumatic speculum, and an anesthetized child), the otoscopic conclusion regarding the presence or absence of ear effusion may vary from observer to observer. Less than half of pediatricians use pneumatic otoscopy. Similar findings have been found in surveys of practicing physicians and residents.

Tympanometry is an objective measure of the condition of the middle ear. It is widely used in specialty clinics for screening and for diagnostic confirmation. The tympanometer displays the change in the acoustic immittance of a 226 Hz transducer tone as the pressure in the ear canal is varied in a range within −300 dekapascals (daPa) to +200 daPa. The classic peaked curve indicates an air-containing middle ear while a classic flat curve is associated with middle ear effusion (assuming an intact TM). Tympanometry is not widely used in primary care offices because of equipment expense and training requirements. The test does require a snug fit between the probe and the ear canal; fitting tightly is not objectionable for older or normal children. However, the pressurization may cause mild discomfort in the presence of an acute infection.

Audiometry often reveals a substantial conductive hearing loss in OME. However, audiometry is expensive and not widely used in primary care practice. Infants and children are not difficult to test by experienced audiologists. Audiometry is important in surgical planning but is too nonspecific for evaluation of effusion type.

Acoustic reflectometry (measuring response of the TM to a 1.8 to 4.4 kHz frequency sweep spectrum) was introduced to meet the need for an objective, simple, and safe clinical method for evaluating the condition of the middle ear. While acoustic reflectometry is indeed simple, safe, and inexpensive, it is too unreliable for making treatment decisions and is used infrequently by physicians.

Accordingly, a more reliable, non-invasive method of diagnosing Otitis Media with Effusion (OME) is needed.

OBJECTS OF THE INVENTION

A first object of the invention is an apparatus and method for detection of acute otitis media (AOM), specifically inflammatory effusion of the middle ear.

A second object of the invention is an apparatus and method for discernment of effusion fluid type in otitis media with effusion (OME) of the middle ear.

A third object of the invention is an apparatus for measurement of fluid viscosity having:

a speculum having an extent, the speculum having a smaller outer and inner diameter on a first end of the extent and a comparatively larger inner and outer diameter on an opposite end of the extent;

the speculum having an ultrasound transducer positioned to generate an ultrasound wave directed out of said first end and into an ear canal and also receive reflected ultrasound energy;

the speculum coupled to an excitation source for displacement of a tympanic membrane with a static or dynamic pneumatic excitation;

the apparatus actuating the tympanic membrane excitation source and measuring tympanic membrane displacement from a phase shift in ultrasound energy reflected from a tympanic membrane;

thereafter forming an estimate of the viscosity of a fluid which may be present on the far side of the tympanic membrane based on the displacement characteristics of a tympanic membrane interacting with the pneumatic excitation.

A fourth object of the invention is an ultrasound signal processor for measurement of the viscosity of a fluid behind a tympanic membrane, the measurement including an excitation resulting in the displacement of the tympanic membrane using the excitation source, the excitation source being sub-audible, audible, or super-audible, the excitation source being either pressure-neutral, pressure-offset, or periodic, the estimate of fluid viscosity performed by measuring the phase shift of reflected continuous wave (CW) or pulsed ultrasound compared to a transmitted waveform phase.

SUMMARY OF THE INVENTION

A speculum tip includes an ultrasound transducer for sending and receiving ultrasound energy through an ear canal and a comparatively low frequency tympanic membrane excitation source. The tympanic membrane excitation source generates a subtle movement of the tympanic membrane during an interval coincident with an ultrasound transmitter delivering acoustic wave ultrasound energy to the tympanic membrane either in CW form or in pulsed form. A receiver for ultrasound reflected from the tympanic membrane measures displacement of the tympanic membrane as a phase change in the received signal when compared to the transmit frequency, thereby indicating a temporal displacement of the tympanic membrane. An analysis of the temporal displacement of the tympanic membrane, as measured by the phase shifts of the reflected ultrasound in response to the pneumatic excitation coupled to the tympanic membrane, in combination with comparison to the temporal displacement or from templates or metrics associated with the delay in and amplitude of response between the excitation stimulus to and ultrasound response from the tympanic membrane, is used to determine the viscosity of the fluid behind the tympanic membrane. Measurement of the viscosity of the fluid behind the tympanic membrane is thereafter used to characterize the type of effusion fluid present in the middle ear as one of: no fluid, serous fluid, or purulent fluid.

BRIEF DESCRIPTION OF THE DRAWINGS

FIG. 2 is a block diagram as in FIG. 1 where the signal processor operates directly on received ultrasound echoes.

FIG. 3 shows waveforms for the system of FIG. 1.

FIG. 4A shows a plot for a sinusoidal excitation applied to an ear canal with a tympanic membrane response with a phase delay and amplitude level.

FIG. 4B shows a plot for a step excitation applied to an ear canal with a tympanic membrane response having a phase delay and amplitude level.

FIG. 4C-1 shows a plot of a sinusoidal TM displacement generating more than +/−180° of phase shift.

FIG. 4C-2 shows the acquired data with phase wrapped from the large phase shifts of FIG. 4C-1.

FIG. 4C-3 shows a plot of an unwrapped phase estimate from FIG. 4C-2.

FIG. 5 shows a CW signal processor for continuous interrogation of a tympanic membrane in response to an excitation generator.

FIG. 5A shows a detail view of the transmit transducer and receive transducer of FIG. 5.

FIG. 6 shows the waveforms for the CW system of FIG. 5.

FIG. 7A is a plot of a sinusoidal excitation source and associated tympanic membrane displacement response.

FIG. 7B is a plot of a step excitation source and associated tympanic membrane displacement response.

DETAILED DESCRIPTION OF THE INVENTION

Figure 1:
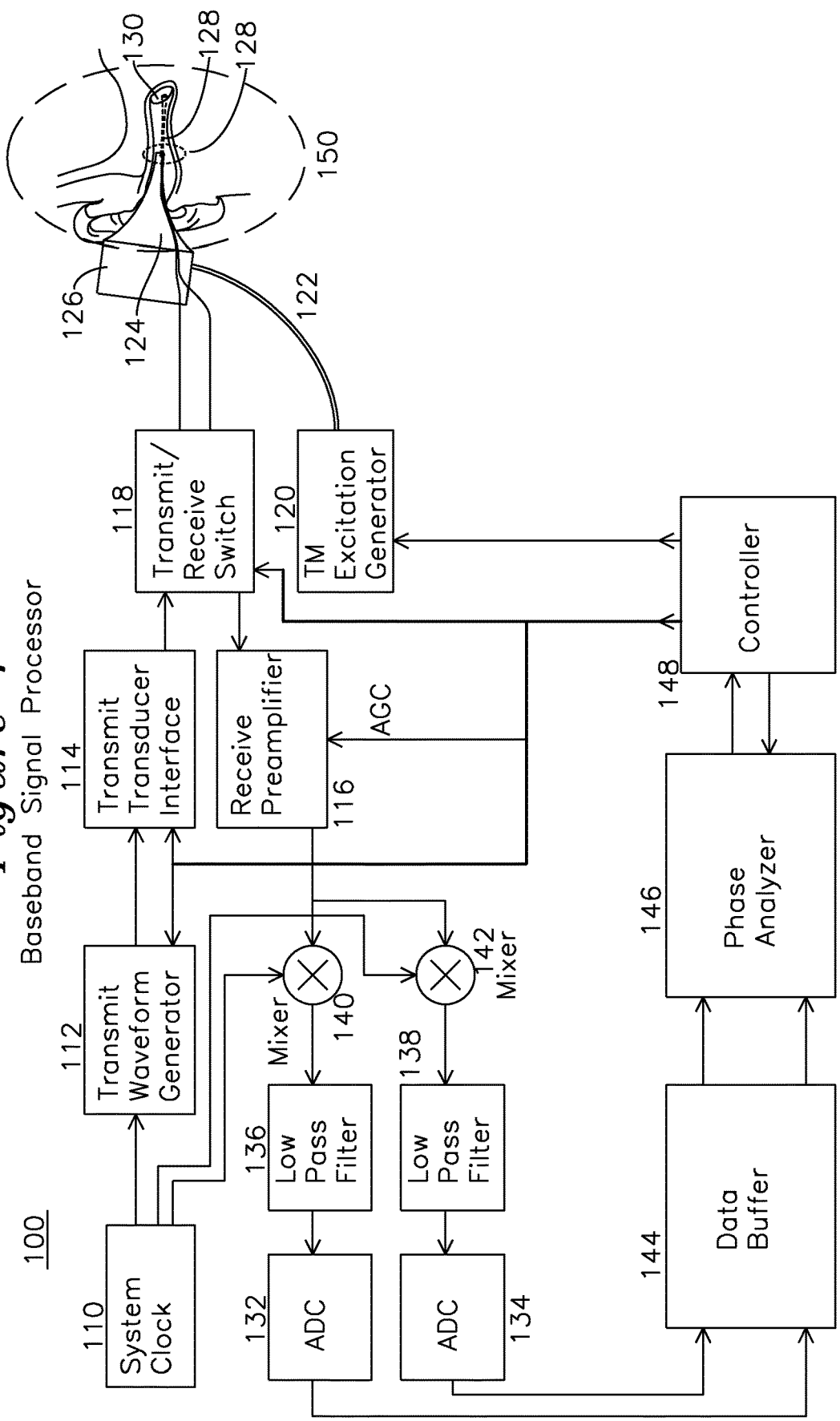
FIG. 1 is a block diagram of a signal processor system for estimating the characteristics of a fluid behind a tympanic membrane.
Figure 1A:
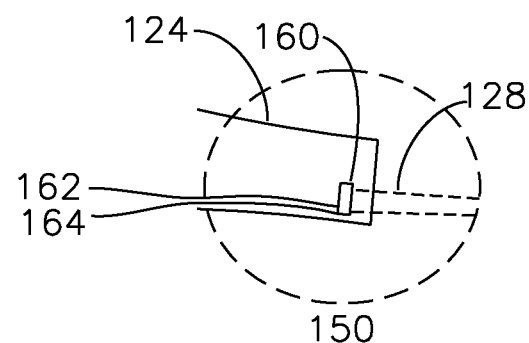
FIG. 1A is a detail view of the speculum tip of FIG. 1.
Figure 1B:
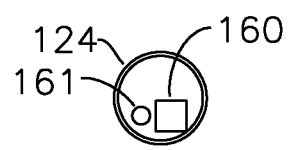
FIG. 1B is a cross section view of FIG. 1A.
Figure 1C:
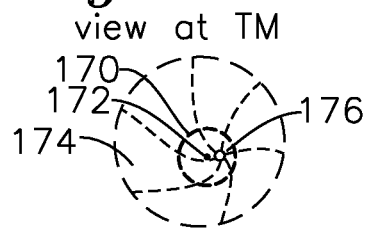
FIG. 1C shows a view of a tympanic membrane and region of illumination and insonification.

FIG. 1 shows a signal processor for an example embodiment of a tympanic membrane characterization system. Region 150 (shown in magnified view FIG. 1A) includes a cross section view of a middle ear and tympanic membrane 130 of a subject being examined. The tympanic membrane 130 is interrogated by an ultrasound beam 128 from an ultrasound transducer 160 (shown in FIG. 1A) which is optionally mounted on the inner surface of a speculum tip 124, and is detachable from an otoscope speculum mounting adapter 126. In one embodiment of the invention, an optical source 161 seen in the FIG. 1B cross section view of FIG. 1A, generates a visual indication the region of insonification by the ultrasound by illumination of a target or region of the tympanic membrane within the ear canal, as seen in FIG. 1C. FIG. 1C shows the view of the tympanic membrane as seen through the speculum, including the tympanic membrane 174, "cone of light" 176, which is a reflective region of the TM which is normal to incident optical illumination and easily located. The optical source 161 may illuminate a small spot 172 indicating the center of the region of ultrasonic insonification 170, or alternatively the spot 172 may be coincident with the ultrasonically insonified region 170. The primary function of the optical source 161 is to provide guidance to a central region 170 of the TM which is most likely to provide diagnostic utility in terms of the analysis of TM displacement as a function of the pressure challenge. The optical source 161 may be a visible spectrum semiconductor laser diode, a light emitting diode, or any other optical emitter which indicates the extent of the region insonified by ultrasound energy and reflecting ultrasound energy for measurement. Preferably, the optical source illuminates a region corresponding to the beam profile of the ultrasonic transducer at the tympanic membrane. The otoscope mounting adapter 126 and speculum tip 124 have a common interior volume which provides for coupling of dynamic pressures from tympanic membrane excitation generator 120 through hose 122 to the ear canal where the air pressures result in displacement of the tympanic membrane 130. The excitation generator 120 may generate pressure variations which are coupled into the ear canal through the speculum tip 126. The excitation generator may produce any suitable pressure modulation for displacement of the tympanic membrane, including a sub-audio frequency below 20 Hz, an audio frequency from 20 Hz to 20 Khz, or a super-audio frequency above 20 Khz. The nature of the pressure excitation generated by the excitation generator may be an impulsive step or delta (impulse) generation, a sinusoidal pressure excitation, a square wave excitation, or any combination of these, and the excitation may be a gated burst or continuous. The pressure excitation may be provided with or without a static positive or negative pressure bias. Speculum tip 124 also has an associated ultrasound transducer 160 with electrical leads 162 and 164 coupled to transmit receive switch 118. Ultrasound transducer 160 generates ultrasound beam 128 which is directed to a central region of the tympanic membrane 130. A controller 148 generates a variety of control signals which are distributed through the signal processor 100. A system reference clock 110 may be derived from a temporally stable clock source, and the reference clock 110 may also be used for demodulation of the received signal. System reference clock 110 is coupled to a transmit waveform generator 112 which generates a pulse train at or near the center frequency of transducer 160, transmit transducer interface 114 performs voltage level shifting and any required amplification before coupling to the transmit/receive switch 118, which couples the waveforms from transmit interface 114 to the ultrasonic transducer 160 via leads 162 and 164. The ultrasound transducer 160 generates and directs the ultrasonic energy in beam 128 to the tympanic membrane. Reflected energy from the tympanic membrane is coupled from the transducer 160 back through leads 162 and 164 to the transmit/receive switch 118, where it is directed to the receive preamplifier 116, which boosts the signal level, and optionally provides automatic gain control through a gain control input from controller 148. The output of the receive preamplifier 116 is applied to quadrature mixers 140 and 142, where a quadrature clock from clock generator 110 at the ultrasound transmitting frequency generates a quadrature output comprising an I (in-phase) baseband channel and Q (quadrature, or 90 degrees separated) baseband channel, which are coupled to identical low pass filters 136 and 138, each of which has a respective analog to digital converter 132 and 134, the output of which is stored in data buffers 144, one for each I and Q channel. The gain control applied to preamplifier 116 is set to place the I and Q signals in an optimum converter range for the A/D converters 132 and 134. When the received signal is mixed with the reference clock in this manner, each transmit pulse generates a single phase value, and over a series of transmit events this sequence of phase differences is used by the phase and amplitude analyzer 146 to estimate the temporal displacement of tympanic membrane 130. In one embodiment of the invention, the transmit clock coupled to the transducer during the transmit interval is derived from system clock 110, which is substantially at the center frequency of the transducer. In an example embodiment where the phase and amplitude analyzer 146 examines primarily the phase of the returned signal, the system clock, at the transmit rate, is also applied to quadrature mixers 140 and 142 during the receive interval to compare the receive signal phase to the system clock (at the original transmit frequency) to generate a phase difference between the transmitted pulse and the reflected pulse. This phase value may be compared over one or more cycles of the receive signal to establish an average phase value for that particular receive interval, and then each phase value from each receive interval assembled to provide a continuous estimate of tympanic membrane displacement, based on the wavelength of the acoustic wave and the phase value measured. In another example embodiment, the phase and/or amplitude analyzer 146 may operate on the amplitude of the received signal, which may be analyzed to provide information about the quality of the phase estimate made from the data (such as from signal to noise metrics), or the amplitude of the signal may be analyzed to provide a metric such as db/Mhz-cm falloff, or the amplitude profile may provide an effusion metric which indicates whether fluid is present behind the tympanic membrane based on the strength and characteristic of the reflection. In general, the effusion metric is any phase or amplitude derived metric from the data presented to the amplitude and phase analyzer 146 which provides a measurement of mobility of the TM, where the mobility is preferentially associated with the presence or absence of effusion in the middle ear for diagnosis of OM. Controller 148 which generates the TM excitation 120 also reads the output of phase and amplitude analyzer 146 over the duration of excitation generator 120 activity, and optionally the amplitude of the reflected signal, to derive a temporal response of the tympanic membrane to the pneumatic excitation provided through speculum tip 124. The pneumatic excitation may be any sub-audio, audio, or super-audio frequency or pulse as previously described.

Figures 1, 4C:
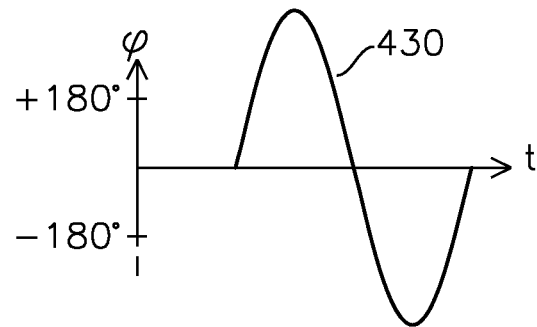
Figures 2, 4C:
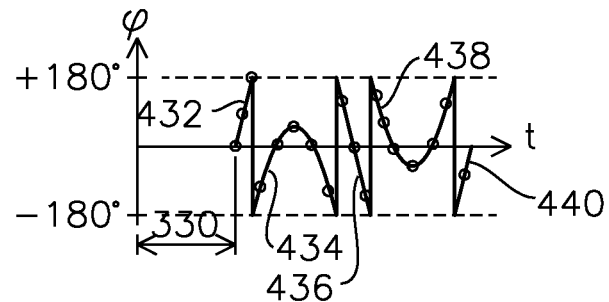

FIG. 2 shows an alternate embodiment of the signal processor of FIG. 1, where the signal processor is performing direct sampling of the RF signal from the transducer, rather than using quadrature mixing to baseband of the RF signal. System clock 210 generates the transmit clock, which is coupled to transmit waveform generator 112. The operation of transmit waveform generator 112, transmit transducer interface 114, transmit receive switch 118, receive preamplifier 116, tympanic membrane excitation source 120 and transducer 160 are as previously described for FIG. 1. The receive preamplifier 116 may be gain controllable, as before, with the gain determined by controller 248 to place the RF signal in optimum A/D converter 232 range. The output of the receive preamplifier 116 is directed to a band pass filter 236 for reduction of the noise bandwidth applied to the ADC 232, which samples at the Nyquist rate of at least 2× faster than the applied signal. For the case of a 1.5 Mhz transducer 160, the Nyquist sampling rate is at least 3 Mhz plus the skirt falloff associated with the bandwidth of the transducer 160, known in the art of signal sampling as the Nyquist sampling criteria. The single channel output of the ADC 232 is applied to a data buffer 244, and a signal analyzer 246 examines phase shifts in the buffered signal to determine phase changes of the RF signal to discern movement of the tympanic membrane. The sequence of phase measurements used to form the phase measurement may be a series of measurements which are inverse-time weighted to increase the effect of recently acquired measurements, or they may be uniformly weighted over a window of phase samples. The use of a weighting coefficients applied to the stream of measurements over a window may provide favorable noise rejection characteristics, and weighting may be chosen to favor signals in the excitation source bandwidth to filter and reduce the effect of noise which is outside the excitation source bandwidth.

Figures 3, 4C:
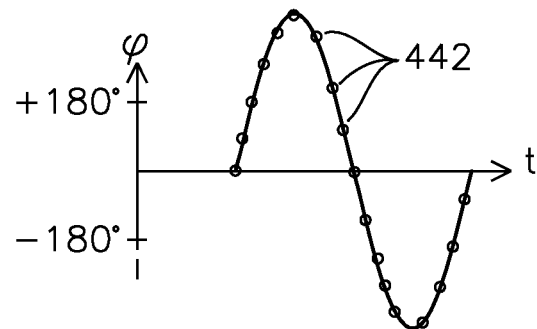

FIG. 3 shows example operation of the ultrasound processor of FIG. 1. In a pulsed RF mode, transmit/receive events provide an estimate of the tympanic membrane position as a series of phase values during a series of repeated interrogation intervals 340, each of which provides a single phase value. System clock waveform 302 operates continuously, and is furnished by system clock generator 110 of FIG. 1. The duration of the event interval 340 is determined by the time-of-flight from the transducer 160 to the tympanic membrane 130 and back to the transducer 160 of FIG. 1. The propagation velocity of ultrasound in air is 330 mt/s (0.33 mm/us). Accordingly, for a 1.5 Mhz transducer, the resultant wavelength of this traveling wave in air is 0.22 mm. The total time of flight for an ultrasound signal 10 mm each direction is then 60 us, so duration 340 may be no less than 60 us in this case. This time of flight interval for a transmit pulse to return as a receive signal after reflection is shown as interval 343 in FIG. 3. The time of flight provides an upper limit to the pulse repetition frequency (PRF) corresponding to the sum of the transmit interval and receive interval. For this example, the transducer with a 1.5 Mhz center frequency will have a 220 u wavelength traveling in air. A displacement of the TM will result in a shortened path from the transducer to the TM, and the reflected signal from the TM back to the transducer will return with a phase shift. Accordingly, the phase and amplitude analyzer observing a phase offset of 180 degrees between transmit clock and received signal compared to a datum phase offset will correspond to a 55 u displacement of the TM. A transmit interval 342 for the transmission of a longer pulse train provides improved signal to noise ratio of the receive signal phase and also extends the return time of flight by the duration 342 of the transmit pulse stream, at the expense of decreased axial resolution, which may be desirable for the case of a discrete moving target such as the tympanic membrane. For a 10 cycle stream at 1.5 Mhz, transmit interval 342 is 6.6 us, and for the reflected signal from a previous transmit burst to not interfere with the new transmit burst, the maximum interval 340 is 66.6 us, which implies a pulse repetition frequency (PRF) of 15 Khz or less. In a limiting case where the TM is 30 us one way time-of-flight distant, and most of the signal energy reflection is at the air/fluid interface of a TM with fluid behind it, and with minimal signal energy reflected from structures beyond the TM, the shortest possible repetition cycle time is 30 us (maximum transmit burst length)+30 us (outgoing time of flight)+30 us (return time of flight). In this idealized scenario, the transducer starts transmitting at t=0 of the repetition cycle. At t=30 us, the first cycle of transmit energy reaches the TM at the same time the transducer is finishing sending the last of the transmit burst. At t=60 us, the first reflected cycle is reaching the transducer and the last cycle of the burst is reflecting from the TM, and at t=90 us, the last cycle of the burst has reached the transducer. In an actual ultrasound system, the PRF will be much lower to account for the required attenuation of multi-path reflection energy which will mix with the TM reflections. In a CW system, separate transmit and receive transducers are used and multipath considerations are ignored. It may be preferable for the system to operate in CW mode in some circumstances, and in pulsed mode in others, depending on the nature of the reflected signal energy. For pulsed mode, it is desired to provide many cycles of transmit energy to improve the phase accuracy of each measurement, particularly where a clear TM reflection boundary is present and most of the signal energy is reflected from the TM. The combined transmit interval and receive interval which determine the PRF may be in the repetition period range of 50 us to 1 ms or more. As multi-path reflections may occur, it may be preferable to reduce the maximum PRF to reduce the effect of ultrasonic reflections from transmit events earlier than the current interval 340, for example. The path length to the TM is also determined by the offset of the transducer from the end of the speculum tip. Although FIG. 1A shows transducer 160 positioned near speculum 124 tip, this distance may vary, and the transducer may be offset inside or outside the speculum tip. In one example of the invention, the transducer is offset substantially 2.5 mm to 5 mm inside the end of the speculum tip as shown in detail 150 of FIG. 1A. For an ultrasound propagation velocity of 0.33 mm/us, when the separation from the transducer to TM is 15 mm, the round trip ultrasound path requires ~90 us, and if the separation distance from transducer to TM is 20 mm, the round trip path requires ~120 us. As an example, for the 20 mm separation distance, a transmit burst length of 15 cycles at 1.5 Mhz would add an additional 10 us, and adding 20 us of settling time for multipath reflections would result in an interval 340 of 150 us, corresponding to a PRF of ~6.67 Khz. Transducer waveform 306 shows the transmit waveform 307 which includes bias and amplitude corrections during the transmit interval 342, and a reduced amplitude receive signal 309 from the tympanic membrane. The received signal 309 also includes the effects of tympanic membrane displacement in the form of a phase change from the system clock, which must be subtracted from any static phase value which may be present. Mixer I and Q outputs, after low pass filtering, are shown as waveforms 308 and 310, respectively. Each 66 us cycle provides a single phase estimate value, which may be considered in polar coordinates using the I and Q outputs. This may be done using a range gate select a time of flight interval corresponding to the region containing a reflection from the tympanic membrane to obtain each sample indicating the instantaneous phase of the tympanic membrane for a particular sample from a transmit event. Each acquired values within an RX interval 344 is averaged or temporally filtered over the temporal region corresponding to the TM reflected response to reach an average phase estimate shown as 311 and 313, respectively, for I and Q waveforms 308 and 310.] A series of such phase estimates are saved, each of these estimates spanning an extent of the Rx interval 344 and which extent corresponds to a reflection from a particular depth. Across multiple data acquisition Rx intervals 344, the samples of IQ are concatenated to construct a time series describing tympanic membrane motion, since phase change over time is attributed to change in distance from the transducer. A succession of these sampled values are collected and compared against a tympanic membrane excitation waveform which is used to form a characterization of the tympanic membrane for a particular excitation waveform.

FIG. 4A shows an example sinusoidal excitation applied to a tympanic membrane, such as a sinusoidal waveform 321 applied using a voice coil diaphragm displacing a volume sufficient to modulate the ear canal pressure by 100 daPa (dekapascals) p-p. Sub-sonic frequencies may require sealing the ear canal, whereas audio frequencies and super-audio frequencies may be sufficiently propagated as audio waves without sealing the ear canal. The sinusoidal ear canal pressure excitation 321 results in a modulation of the tympanic membrane, which is shown as phase plot 332, as the modulation in tympanic membrane position corresponds to a change in the phase of the return signal. Each discrete circle of waveform 332 represents a sample point such as a polar conversion of average values for I 311 and Q 313. In one example embodiment of the invention, a series of sinusoidal modulation excitation 321 frequencies are applied, each with a different period 322, and the delay in response 330 and peak phase amplitude are used in combination to estimate the viscosity of the fluid behind the ear. Since each 360 degree phase change of the 1.5 Mhz transmit pulse corresponds to lambda/2=0.11 mm, a phase change of +/−180 degrees total as shown in plot 332 would correspond to 0.11 mm peak to peak displacement of the tympanic membrane. By applying a series of audio and sub-audio tones with various cycle times 322 and measuring the phase response as shown in plot 332, it is possible to estimate viscosity of the fluid behind the tympanic membrane. For example, an exemplar effusion metric measurement associated with the changed density or viscosity of the fluid could be an associated change in tympanic response time. In this manner, a frequency domain response of the tympanic membrane may be made using a series of excitations 321 and measuring a series of tympanic membrane responses 332.

The series of FIGS. 4C-1, 4C-2, and 4C-3 show the effect of reconstructing TM displacements when the received signal phase exceeds λ/2 (180°, corresponding to a λ/4 TM displacement). FIG. 4C-1 shows a received signal 430 with displacement-associated phase excursions which exceed λ/2 (180°). Because phase excursions greater than 180° wrap to −180°, the series of samples of FIG. 4C-2 wrap and produce the series of samples shown, with samples of individual segments 432, 434, 436, 438, and 440. If a sufficiently high sample rate is used, it is possible to "unwrap" the samples as shown in FIG. 4C-3, to provide the original phase information. These techniques are well known in the prior art of Doppler signal reconstruction.

Whereas FIG. 4A shows a sinusoidal excitation which may be provided in a series of such excitations to generate a phase vs. frequency response plot of the TM displacement from the series of measurements, FIG. 4B shows a time domain step response equivalent of FIG. 4A, where a step pressure excitation 362 of 50 daPa peak is applied to the ear canal, which generates the phase response 372 of the return signal from the tympanic membrane. It is similarly possible to characterize the tympanic membrane response based on a time delay 374 and amplitude response (shown as 180 degrees) for phase response plot 372, corresponding to 0.11/2 mm displacement. The phase unwrap techniques described in the series of FIG. 4C-1, 4C-2, 4C-3 may similarly be applied to the samples of waveform 372 of FIG. 4B to reconstruct phase shifts in excess of +/−180°.

The signal processing of FIG. 2 operates in a similar manner as was described for FIG. 3, however the transducer reflection 306 is directly sampled and compared with a reference clock to determine the phase changes associated with the tympanic membrane movement, for example by multiplying the reference clock with the received signal over a receive signal averaging time, and integrating this value over the duration of the receive signal to estimate a phase value for one receive interval. In a similar manner, this will result in the generation of response waveform 332 from excitation source 321 interacting with the tympanic membrane, as described for FIG. 4A, or response waveform 372 from excitation source 362 interacting with the tympanic membrane.

FIG. 5 shows another embodiment of the invention for CW operation. The signal processor of FIG. 5 operates as in FIG. 1, and with the same block descriptions operative as was present in FIG. 1, however the transmit interface 114 is directly coupled via leads 502/504 to a transmit transducer shown in detail view of FIG. 5A as 524 and generating transmit beam 526, which is coincident on the tympanic membrane with the receive beam profile 528 of receive transducer 530, which conveys the receive signal using leads 506/508 to receive amplifier 116, where the signal processing occurs as described previously for FIG. 1, however, the system of FIG. 5 operates continuously, with the transmitter continuously transmitting, and the receiver baseband signal being continuously received. This operation is advantageous for detection of signal bandwidth which exceeds the pulsed transmit configuration described in FIG. 3. Because the CW transmit signal results in a standing DC offset at the receive mixers 140 and 142, it is desired to provide electronic isolation between transmit element 524 and receive element 530.

FIG. 6 shows waveform plots for the baseband CW system of FIG. 5. The system clock 110, transmit waveform generator 112, and transmit transducer interface 114 generate a biased transducer CW signal waveform 602 of FIG. 6, which is applied to the transmit transducer 524 of FIG. 5, and the receive transducer 530 of FIG. 5 generates receive signal 608 of FIG. 6. The outputs of the I and Q channel low pass filters 136 and 138, respectively, are shown as waveforms 614 and 616. The phase unwrapping techniques described previously may be applied to these waveforms as well, where the detected phase crosses the +/−180° boundary and wraps to the opposite boundary.

FIGS. 7A and 7B show CW output 714 for an excitation 702, and the sample points of 332 and 372 of FIGS. 4A and 4B are not present, as the CW system of FIG. 5 is not subject to the baseband Nyquist sampling limitations of the pulsed dopper system of FIGS. 2 and 3, provided that the mixer output is sampled at a sufficiently high rate to satisfy the Nyquist criteria for phase changes at the mixer output.

The transducer types for 130 of FIGS. 1 & 2, and 524 and 530 of FIG. 5A may be any of capacitive micromachined ultrasonic transducer (cMUT), or piezoelectric transducers, for example, formed with the piezoelectric material PZT.

The example embodiments for the signal processors have shown embodiments of a pulsed Doppler system of FIGS. 1 and 2, and a CW Doppler system of FIG. 5. Each of these systems can be practiced using direct RF sampling, as shown in FIG. 2, where a bandpass filter is operative to reduce the noise bandwidth of the system to $e_n = \sqrt{4kTBR}$, commonly expressed as nanovolts per root hertz, where K is the Boltzmann constant $1.38*10^{-23}$;

T is the temperature of the system, assumed to be 300° K;

B is the bandwidth of the sampled signal (either the bandwidth of the bandpass filter 236 of FIG. 2, or bandwidth of the low pass filter 136/138 of FIGS. 1 and 5;

and R is the resistance generating the Johnson noise, typically 50 ohms.

In an ideal system Johnson noise is generated by transducer 160 and preamplifier 120 of FIG. 1, and this noise is frequency-limited to reduce its effect on system measurements. The noise floor for a 50 ohm system is 0.9 nV/√Hz. It is typically easier to perform narrowband filtering on a baseband signal such as the low pass filters 136 and 138 of FIG. 1 than the bandpass filter 236 of FIG. 2. For example, a first order band pass filter 236 for a 1.5 Mhz system might have a 3 db bandwidth of 1 Mhz, whereas the desired signal content is below 1 Khz, which is difficult to incorporate into bandpass filter 236, but simple to incorporate into low pass filter 136. Accordingly, the sample noise floor for 1 Khz baseband system would 28 nV rms whereas the 1 Mhz bandwidth direct sampling system would be 30× higher, or 900 nV rms with the same signal energy. The noise factor of the system (typically governed by the first few elements in the receive chain) is managed separately, as it would scale the noise floor by the noise factor, so a 6 dB noise factor would approximately double both of the above rms noise floor values.

The invention may be practiced many different ways. In one embodiment, the phase and amplitude analyzer produces an effusion metric which is a characterization of the sequence of phase measurements from the ultrasound reflection from the tympanic membrane in combination with the displacement of the tympanic membrane from the tympanic membrane excitation source. The effusion metric which is derived from the response of the tympanic membrane may provide an indication of whether the tympanic membrane has an air boundary indicating no effusion, a watery fluid boundary, or a purulent fluid boundary. When fluid is detected, one effusion metric may be a viscosity estimate, another effusion metric may be a scattering metric.

The components of the system are shown in block diagram form for clarity in understanding the invention. Certain components are indicated as present in a speculum tip, for clarity of understanding the operation of the invention. It should be understood that these components may be located anywhere, including inside or outside the speculum tip, or alternatively the objects of the invention may be accomplished with the described structures and no speculum tip at all. Alternatively, the speculum tip may be removable with the various structures stationary or removable, including any optical element for viewing of a tympanic membrane, ultrasound transducer, or optical source. The particular arrangement of the elements with respect to the speculum tip is shown for clarity and to illustrate one example of the invention.

The excitation generator may be a manual bulb operated by a clinician, an air displacement generator producing alternating pressure, step pressure, or air puffs. The excitation generator output may be sealed to the ear canal or unsealed and using a puff of gas such as atmospheric air or other suitable gas.

The estimate of tympanic membrane deflection may be derived from a velocity, an acceleration, or any other metric associated with deflection over time.

Various aspects of the invention may be practiced, as recited below:

A signal processor for detection of air or fluid behind a tympanic membrane, and further estimating an effusion metric of a fluid when present, the signal processor comprising:

a speculum tip having an ultrasound transducer for coupling ultrasound energy into an ear canal and to a tympanic membrane;

an excitation generator producing sub-audio, audio, or super-audio excitation coupled into said speculum tip and having sufficient amplitude to cause a measurable deflection in a tympanic membrane;

a transmitter coupled to said ultrasound transducer during a transmit interval;

a receiver coupled to said ultrasound transducer during a receive interval which follows said transmit interval;

a phase and/or amplitude analyzer comparing the phase of a transmit signal of said transmit interval to a phase and/or amplitude of a receive signal during said receive interval to estimate a tympanic membrane deflection;

said signal processor deriving a metric from said phase and amplitude analyzer by comparing said tympanic membrane deflection with said excitation generator output;

said effusion metric indicating whether said receive signal is a reflection from a membrane structure which includes reflections from air or from fluid, and optionally characterizing a fluid when detected.

A signal processor where said speculum tip includes an optical source which indicates a region of insonification of ultrasound from said ultrasound transducer.

A signal processor where said speculum tip provides at least one optical element for direct viewing of a tympanic membrane to be characterized.

A signal processor where said speculum tip provides an aperture through which image capture may be performed for providing a captured image to a display.

A signal processor where a camera is positioned in said aperture.

A signal processor where said aperture provides an optical path to an optical viewing port.

A signal processor where said speculum tip is removable.

A signal processor where said speculum tip includes said ultrasound transducer.

A signal processor where said excitation generator generates at least one of: sinusoidal, impulse, steady state, or periodic sub-audio, audio, or super-audio excitation.

A signal processor where said phase and amplitude analyzer is operative on received acoustic energy from said transducer at a natural center frequency of said transducer.

A signal processor where said phase and amplitude analyzer is operative on received acoustic energy from said transducer at a baseband frequency spectrum, said baseband frequency spectrum formed by mixing said receive signal with a carrier frequency which is at substantially the center frequency of said transmitter.

A signal processor where said transmitter generates a transmit waveform which includes an excitation voltage signal at a center frequency of said transducer during said transmit interval.

A The signal processor where the sum of said transmit interval and said receive interval is greater than 50 microseconds and less than 1 millisecond.

A signal processor where said phase and amplitude analyzer determines a weighted or unweighted average phase with respect to a transmit clock.

A signal processor where said metric is a temporal phase change between a received signal from said transducer during said receive signal interval and a transmit clock which is operative during said receive interval.

A signal processor where said metric is a phase relationship between a mixer output baseband signal and said excitation generator output.

A signal processor of claim 1 where said metric is derived from a temporal phase change in said receive signal and said excitation generator output.

A signal processor where said ultrasound transducer generates a periodic burst of transmit signal energy.

A signal processor where said ultrasound transducer generates continuous transmit signal energy.

A signal processor where said phase and amplitude analyzer is operative on received signals to identify a region of first reflection from a tympanic membrane, and thereafter characterizes a fluid behind said identified region as either air or liquid.

A The signal processor where, when said fluid behind said identified region is liquid, determines a viscosity of said fluid using a phase and amplitude response associated with said measurable deflection.

A signal processor for characterizing a temporal response from an eardrum, the signal processor having:

an excitation generator producing sub-audio, audio, or super-audio excitation for application to a tympanic membrane to cause a displacement;

a transducer for launching acoustic waves towards a tympanic membrane and receiving reflections from a tympanic membrane;

a visual indicator to allow the direction of acoustic waves from said transducer to a region of interest on a tympanic membrane;

an ultrasound transmitter operative during a transmit interval and coupling a gated frequency burst to said transducer;

an ultrasound receiver operative during a receive interval and coupled to said transducer;

a phase and amplitude detector comparing the phase of a transmit clock to a receive signal from said ultrasound receiver and generating a phase output;

a response analyzer comparing said phase output to the excitation generator output, said response analyzer determining a viscosity of a fluid adjacent to a tympanic membrane by comparison of said phase output and said excitation generator output.

A signal processor where said transducer is at least one of a capacitive micro-machined ultrasound transducer (cMUT) or a piezoelectric transducer.

A signal processor where said excitation generator is at least one of a voice coil actuator, or a moving diaphragm.

A signal processor where said visual guide is at least one of: a laser diode, light emitting diode, or optical indicator which illuminates a region corresponding to a beam profile from said ultrasonic transducer.

A signal processor where said ultrasound transmitter has a repetition rate of less than 15 Khz.

A signal processor where said phase and amplitude detector is a baseband mixer generating an output after a low pass filter.

A signal processor where said phase and amplitude detector is operative at a center frequency of said transducer.

A signal processor where said response analyzer compares said phase output and said excitation generator output over a plurality of sample points over a duration of time when said excitation generator is operative.

A signal processor where said receive interval and said transmit interval are concurrent intervals.

A signal processor where said receive interval and said transmit interval are exclusive intervals.

We claim:

1. A device for characterizing a tympanic membrane, the device comprising:
   an excitation generator configured to produce an excitation comprising a pressure modulation in air for application to the tympanic membrane to cause a displacement;
   a transducer configured to transmit acoustic waves towards the tympanic membrane during a transmit interval and to receive reflected acoustic waves from the tympanic membrane during a receive interval;
   an optical source configured to provide a visual indication of a region of insonification on the tympanic membrane, thereby allowing direction of the acoustic waves from the transducer to a region of interest on the tympanic membrane;
   a phase and amplitude detector configured to receive a phase and an amplitude of the reflected acoustic waves, compare a phase of the transmit signal to the phase of the reflected acoustic waves, and generate a phase output; and
   a response analyzer configured to compare the phase output to the excitation and determine one or more of a viscosity of a fluid adjacent to the tympanic membrane or a mobility of the tympanic membrane based on the comparison.

2. The device of claim 1, wherein the transducer is a capacitive micro-machined ultrasound transducer (cMUT) or a piezoelectric transducer.

3. The device of claim 1, wherein the excitation generator is a voice coil actuator or a moving diaphragm.

4. The device of claim 1, wherein the optical source is a laser diode or a light emitting diode.

5. The device of claim 1, wherein the transducer has a repetition rate of less than 15Khz.

6. The device of claim 1, wherein the phase and amplitude detector comprises a baseband mixer.

7. The device of claim 1, wherein the optical source is configured to illuminate a region encompassing to an acoustic beam profile of the transducer.

8. The device of claim 1, wherein the response analyzer is configured to compare the phase output to the excitation over a plurality of sample points.

9. The device of claim 1, wherein the receive interval and the transmit interval are concurrent intervals of time.

10. The device of claim 1, wherein the receive interval and the transmit interval are exclusive intervals of time.

11. The device of claim 1 further comprising a transmit/receive switch and a preamplifier coupled to the transducer.

12. The device of claim 11 further comprising one or more of a mixer, a low pass filter, or an analog to digital converter coupled to the transducer.

13. The device of claim 1, wherein the response analyzer is configured to form an effusion metric by measuring a phase delay for each frequency of the excitation generator.

14. The device of claim 13, wherein the effusion metric distinguishes between no effusion, serum effusion, or purulent effusion.

15. The device of claim 1, wherein the response analyzer is configured to form an effusion metric by measuring an amplitude response for each frequency of the excitation generator, wherein the presence and type of effusion is determined by a frequency of the excitation generator for which a reduction in an amplitude response is detected.

16. A device for characterizing a tympanic membrane, the device comprising:
   a speculum tip configured to be inserted into an ear canal;
   an excitation generator coupled to the speculum tip and configured to generate an excitation waveform comprising a pressure modulation in an air volume to cause a displacement in the tympanic membrane;
   an ultrasound transducer distinct from the excitation generator and positioned in the speculum tip, wherein the ultrasound transducer is configured to transmit ultrasound energy and to receive reflected ultrasound energy from the tympanic membrane;
   a transmit/receive switch coupled to the ultrasound transducer;
   a receiver configured to amplify reflected ultrasound energy received from the ultrasound transducer to form a received signal, wherein the received signal comprises a phase and amplitude of the reflected ultrasound energy,
   a detector configured to generate a plurality of phase and amplitude measurements each comprising a difference between the transmitted ultrasound energy and the received signal,
   a signal analyzer configured to compare the plurality of phase and amplitude measurements to the excitation waveform and form an effusion metric.

17. The device of claim 16, wherein the plurality of phase and amplitude measurements are over a plurality of excitation signal frequencies.

18. The device of claim 17, wherein the plurality of excitation signal frequencies are applied, each with a different period, to determine a frequency where a peak phase amplitude occurs.

19. The device of claim 18, wherein the frequency where the peak phase amplitude occurs is associated with a viscosity of a fluid behind the tympanic membrane.

20. The device of claim 19, wherein the frequency where the peak phase amplitude occurs determines the viscosity of the fluid as that of air, serum fluid, or purulent fluid.

21. The device of claim 16, wherein the plurality of phase measurements are made using a continuous wave (CW) transmit signal or a pulsed transmit signal.

22. The device of claim 16, wherein the ultrasound transducer is at least one of a capacitive micro-machined ultrasound transducer (cMUT) or a piezoelectric transducer.

23. The device of claim 16, wherein the excitation generator is at least one of a voice coil actuator or a moving diaphragm.

24. The device of claim 16, wherein the signal analyzer is configured to compare phase and amplitude is operative using a step change in excitation generator volume to the speculum tip.

25. The device of claim 16, wherein the signal analyzer is configured to compare phase and amplitude is operative using a sinusoidal frequency change in excitation generator output coupled to the speculum tip.

26. The device of claim 16, wherein the detector further comprises a baseband mixer.

27. The device of claim 16, wherein the signal analyzer is configured to compare the phase output to the excitation over a plurality of sample points.

28. The device of claim 16, wherein the ultrasound transducer is configured to transmit the ultrasound energy during a transmit interval, wherein the transducer is configured to receive the reflected ultrasound during a receive interval, and wherein the receive interval and the transmit interval are concurrent intervals of time.

29. The device of claim 16, wherein the ultrasound transducer is configured to transmit the ultrasound energy during a transmit interval, wherein the transducer is configured to receive the reflected ultrasound during a receive interval, wherein the receive interval and the transmit interval are exclusive intervals of time.

30. The device of claim 16, wherein the response analyzer is configured to form an effusion metric by measuring a phase delay for each frequency of the excitation generator.

31. The device of claim 30, wherein the effusion metric distinguishes between no effusion, serum effusion, or purulent effusion.

\* \* \* \* \*

UNITED STATES PATENT AND TRADEMARK OFFICE
CERTIFICATE OF CORRECTION

PATENT NO. : 10,660,604 B2
APPLICATION NO. : 14/797181
DATED : May 26, 2020
INVENTOR(S) : Mark A. Moehring et al.

It is certified that error appears in the above-identified patent and that said Letters Patent is hereby corrected as shown below:

In the Claims

In Claim 1, Column 15, Line 22, please change "signal" to -- acoustic waves --

In Claim 7, Column 15, Line 42, please change "encompassing" to -- corresponding --

In Claim 13, Column 15, Line 56, please delete the second space between "the" and "response"

In Claim 16, Column 16, Line 23, please insert -- and -- after "signal,"

In Claim 18, Column 16, between Lines 30 and 31, please delete the second space between "of" and "excitation"

In Claim 19, Column 16, between Lines 34 and 35, please delete the second space between "where" and "the"

In Claim 24, Column 16, Line 50, please delete "is operative" after "amplitude"

In Claim 25, Column 16, Line 54, please delete "is operative" after "amplitude"

In Claim 30, Column 17, Line 7, please change "response" to -- signal --

Signed and Sealed this
Sixth Day of July, 2021

Drew Hirshfeld
*Performing the Functions and Duties of the
Under Secretary of Commerce for Intellectual Property and
Director of the United States Patent and Trademark Office*